United States Patent
Lai et al.

(10) Patent No.: US 6,886,570 B2
(45) Date of Patent: May 3, 2005

(54) HYBRID DENTAL FLOSSER AND TOOTHBRUSH

(76) Inventors: Ming Lai, P.O. Box 10845, Pleasanton, CA (US) 94588; Meijuan Yuan, P.O. Box 10845, Pleasanton, CA (US) 94588

( * ) Notice: Subject to any disclaimer, the term of this patent is extended or adjusted under 35 U.S.C. 154(b) by 0 days.

(21) Appl. No.: 10/453,421

(22) Filed: Jun. 2, 2003

(65) Prior Publication Data

US 2004/0035439 A1 Feb. 26, 2004

Related U.S. Application Data

(60) Provisional application No. 60/405,119, filed on Aug. 22, 2002.

(51) Int. Cl.$^7$ .............................................. A45D 44/18
(52) U.S. Cl. ....................................... 132/309; 132/327
(58) Field of Search ................................. 132/322, 323, 132/324, 325, 326, 327, 309; 15/22.1, 22.2, 22.4

(56) References Cited

U.S. PATENT DOCUMENTS

| | | | | |
|---|---|---|---|---|
| 4,880,382 A | * | 11/1989 | Moret et al. ................. | 433/118 |
| 5,033,150 A | * | 7/1991 | Gross et al. .................. | 15/22.1 |
| 5,253,382 A | * | 10/1993 | Beny ........................... | 15/22.1 |
| 5,343,883 A | * | 9/1994 | Murayama ................... | 132/322 |
| 5,361,446 A | * | 11/1994 | Rufo .......................... | 15/167.1 |
| 5,400,811 A | * | 3/1995 | Meibauer ..................... | 132/322 |
| 5,921,254 A | * | 7/1999 | Carlucci et al. ............. | 132/322 |
| 6,047,711 A | * | 4/2000 | Wagner ....................... | 132/322 |

* cited by examiner

Primary Examiner—Kevin Shaver
Assistant Examiner—Stephanie L. Willatt

(57) ABSTRACT

The present invention contemplates to adapt the shape and movement of a popular manual flosser into an automatic flosser to minimize the learning time required for manipulating automatic dental flossing. The present invention also contemplates to combine the automatic flosser with a popular automatic toothbrush and thus to make the automatic flosser available to the users with substantially no additional cost to the automatic toothbrush. The present invention further contemplates to accomplish circular oscillation of the toothbrush bristles of the automatic toothbrush and side-to-side vibration of the dental floss of the automatic flosser.

17 Claims, 11 Drawing Sheets

HYBRID DENTAL FLOSSER AND TOOTHBRUSH

This application claims the benefit of U.S. provisional application No. 60/405,119, filed on Aug. 22, 2002.

TECHNICAL FIELD

The present invention relates to a motorized device and method for dental flossing and tooth-brushing. In particularly, the present invention relates to a hybrid unit of automatic dental flosser and automatic toothbrush, of which the automatic flosser drives a piece of dental floss to vibrate from side to side longitudinally while the automatic toothbrush drives the bristles to oscillate back and forth rotationally.

BACKGROUND

The clinic benefit of dental flossing is well known. If you live in the United States, the most frequent advice you may get from your dentist is to floss once a day. Traditional manual flossing is, however, time consuming and less effective. Besides, many of us find manual flossing too difficult to manipulate.

Automatic flosser, i.e. automatic dental flossing device, has been the subject of numerous of patents; some of them are listed as references in this application. However, automatic flossers have so far very limited acceptance in the market place.

There are two obvious obstacles for broad market acceptance of automatic flossers. First, substantial learning time is usually required for one to become familiar with manipulation of an automatic flosser and to see its benefit. Actually, dental flossing is never an easy job for most of us. Any new flosser or new flossing procedure will take time and practice for one to learn.

Second, commercially available automatic flossers are typically sold for $30 to $80 per unit in the US market. These prices are some 10 to 50 times of what one may spend for dental floss or manual flossers. Because the usefulness and benefit of a new automatic flosser are usually not obvious, not many customers are likely to pay $30 to $80 to try something new but uncertain.

In comparison, automatic toothbrushes have found their way to gain popularity in the past several years. Automatic toothbrushes were used to sell for some $30 to $80 per unit in the US market and had rather limited popularity. The market of automatic toothbrushes has become flourishing since Crest introduced its SpinBrush sold for about $5 each.

SUMMARY

The present invention contemplates a new and improved automatic flosser to overcome the above-identified obstacles. The present invention contemplates to adapt the shape and movement of a popular manual flosser into an automatic flosser to minimize the learning time required for manipulating automatic dental flossing. The present invention also contemplates to combine the automatic flosser with a popular automatic toothbrush and thus to make the automatic flosser available to the users with substantially no additional cost to the automatic toothbrush. The present invention further contemplates to accomplish circular oscillation of the toothbrush bristles of the automatic toothbrush and side-to-side vibration of the dental floss of the automatic flosser.

The combined unit of automatic flosser and toothbrush consists of a disposable floss holder, a detachable toothbrush head, and a common driving handle. This combined unit is intended to pack and sell at a price of the automatic toothbrush. Package of multiple disposable floss holders is to sell separately. This way, customers are encouraged to buy the automatic toothbrush with a free disposable floss holder and the automatic flossers become readily available for a free trial to those customers.

The combined unit accomplishes a circular oscillation of the toothbrush bristles, which is the most popular motion of commercially available automatic toothbrushes. Meanwhile, the combined unit accomplishes a longitudinally reciprocal movement of the dental floss, which is a more familiar motion with manual flossers. In one embodiment, the disposable floss holder remains stationary while the dental floss is moving back and forth between two tines of the automatic flosser. This design allows the dental floss to have large travel for more effective dental flossing. In another embodiment, the floss holder securing a piece of dental floss swings from side to side to move the dental floss longitudinally and reciprocally. This design enables the use of a disposable floss holder free of any moving part, and thus the disposable floss holder can be made simple and cheap.

The driving mechanism of the driving handle adapts designs having similar complicity to those found in popular automatic toothbrushes. The disposable floss holder can be made from a single piece of plastic using mold injection process. Therefore, the combined unit of the automatic flosser and toothbrush can be made and sold at substantially the same price as those popular automatic toothbrushes, i.e. about $5 in the US market.

Accordingly, an objective of the present invention is to provide a new and improved automatic dental flosser employing a disposable floss holder that stays stationary while the floss is dragged to move back-and-forth longitudinally.

Another objective of the present invention is to provide a new and improved automatic dental flosser employing a disposable floss holder that is made of a single piece of plastic.

A further objective of the present invention is to provide a new and improved automatic dental flosser sharing the same driving handle such that the combined unit of automatic flosser-toothbrush can be sold at substantially the same price of the automatic toothbrush.

Another further objective of the present invention is to provide a new and improved automatic flosser-toothbrush employing a hybrid motion, of which the floss holder is driven to swing side to side while the toothbrush bristles are driven to oscillate rotationally.

The above and other objectives and advantages of the invention will become more apparent in the following drawings, detailed description, and claims.

DETAILED DESCRIPTION

Figure 1:
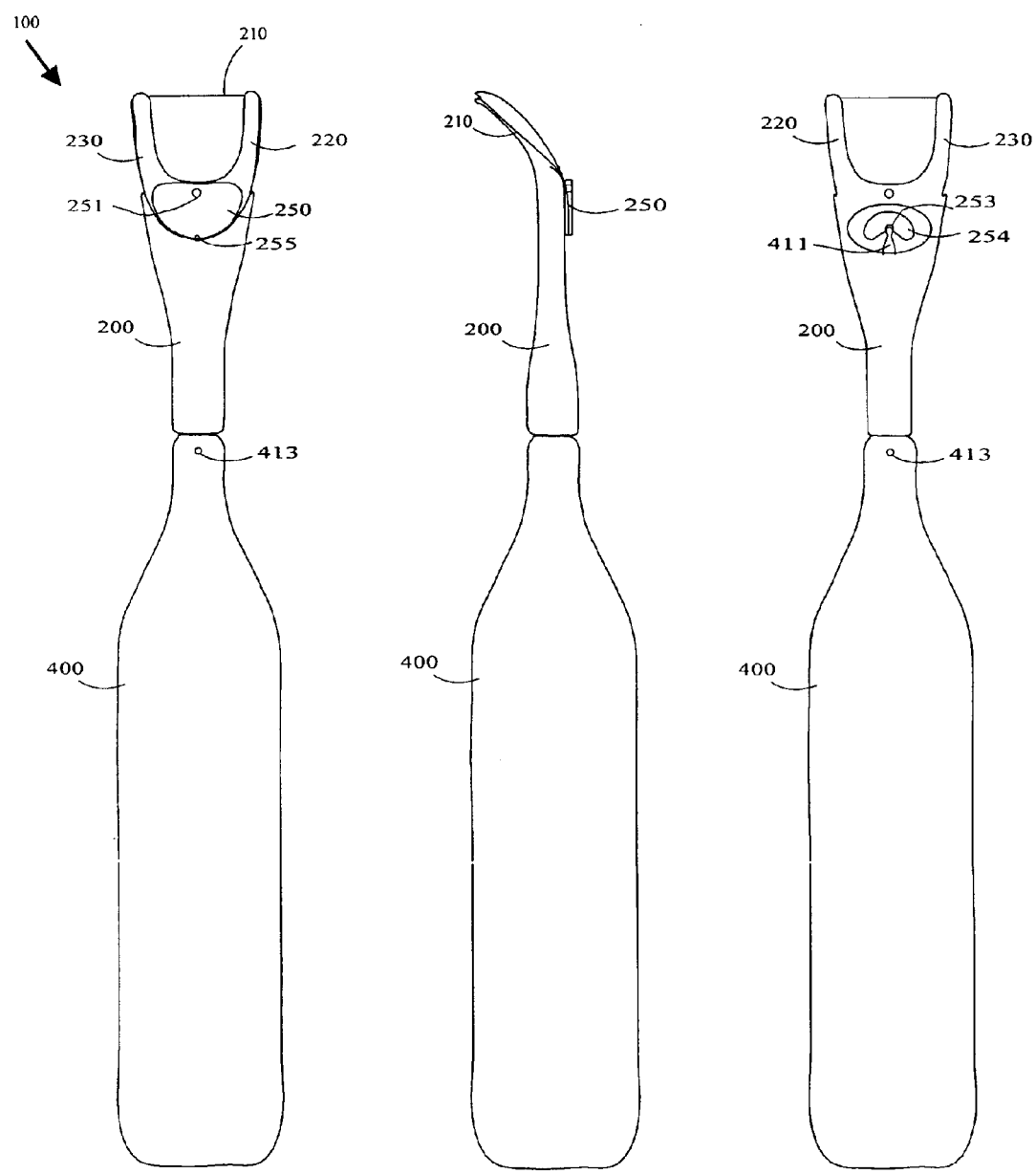
FIG. 1 shows an automatic dental flosser, in accordance with the present invention.

FIG. 1 shows an automatic dental flosser 100, in accordance with the present invention. The automatic dental flosser 100 consists of a disposable floss holder 200 attached onto a driving handle 400. The disposable floss holder 200 holds a loop of dental floss 210 between two tines 220 and 230. As described below, a driving mechanism housed inside the driving handle 400 drives a driving shaft 411 to oscillate from side to side. The driving shaft 411 then drives a rotatable element 250 to swing back and forth with respect to the disposable floss holder 200. As a result, the loop of dental floss 210 is drag to slide back and forth between the two tines 220 and 230 for dental flossing, while the disposable floss holder 200 stays stationary with respect to the driving handle 400.

Figure 2:
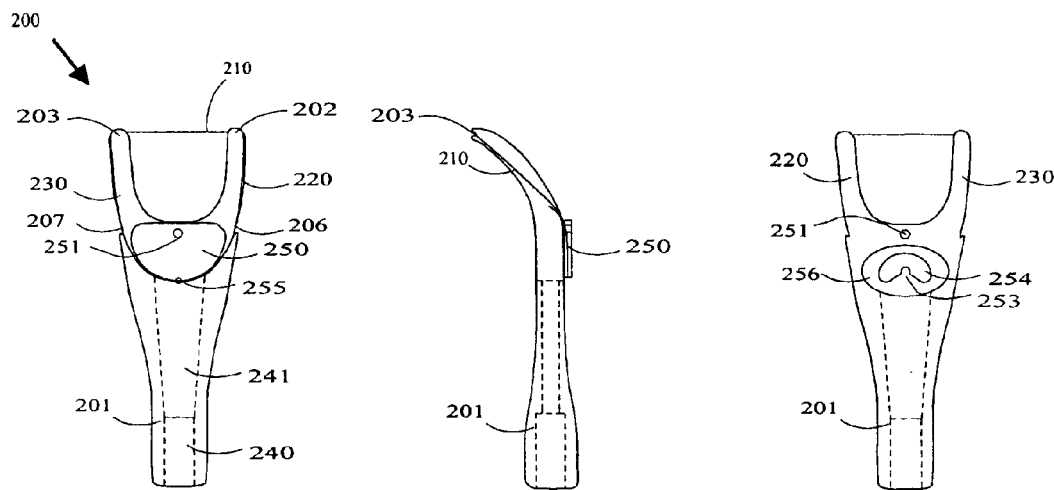
FIG. 2 shows a first embodiment of a disposable floss holder.

FIG. 2 shows a first embodiment of a disposable floss holder 200, in accordance with the present invention. The disposable floss holder 200 is shown in front, side, and back view. The disposable floss holder 200 consists of a holder body 201, a rotatable element 250, and a loop of dental floss 210. The rotatable element 250 is rotatable with respect to the holder body 201 via a pin-and-hole structure 251.

One point 255 of the rotatable element 250 is tied to the loop of dental floss 210. The rotatable element 250 is affixed with an engagement element 254 that has a notch 253, which can be engaged with the tip of a driving shaft 411 from the driver handle 400, as shown in FIG. 1. There is an opening 256 on the holder body 201 to receive the engagement element 254 and to allow the engagement element 254 to rotate within a range around the pin-and-hole structure 251. As the driving shaft 411 of the driving handle 400 oscillates from side to side, it drives the rotatable element 250 to swing back and forth with respect to the holder body 201.

The pin-and-hole structure 251 has two possible configurations. The first configuration is to have a hole on the holder body 201 and a pin on the rotatable element 250 to insert into the hole. The other configuration is to have a pin on the holder body 201 and a hole on the rotatable element 250 to receive the pin. This way the rotatable element 250 is rotatable around the pin-and-hole structure 251.

The loop of dental floss 210 is held between the two tines 220 and 230 through holding slots 202, 203, 207, and 206. The loop of dental floss 210 is free to slide back and forth around these holding slots 202, 203, 207 and 206. When the rotatable element 250 swings back and forth around the pin-and-hole structure 251, it drags the loop of dental floss 210 to move back and forth between the two tines 220 and 230.

The implement of the rotatable element 250 with the engagement element 254 is for two advantages. First, it can enlarge the travel of the dental floss 210 between the two tines 220 and 230, in comparison with the displacement of the driving shaft 411. Second, it provides a simple engagement to transfer the oscillation of the driving shaft 411 to the back-and-forth movement of the dental floss 210 with the floss holder remaining stationary. Preferably, the first end 412 of the driving shaft 411 has a peak-to-peak oscillation of approximately 2 to 3 mm and the dental floss 410 has a back-and-forth travel of about 4 to 8 mm.

There is a mounting hole 240 on the second end of the holder body 201. This hole 240 is used to attach and to secure the floss holder 200 onto the driving handle 400. There is also a hole 241 connecting between the mounting hole 240 and the opening 256. As shown in FIG. 1, this hole 241 enables the driving shaft 411 of driving handle 400 to engage with the notch 253 of the engagement element 254 and thus to drive the rotatable element 250 to swing back and forth around the pin-and-hole structure 251.

Figure 3:
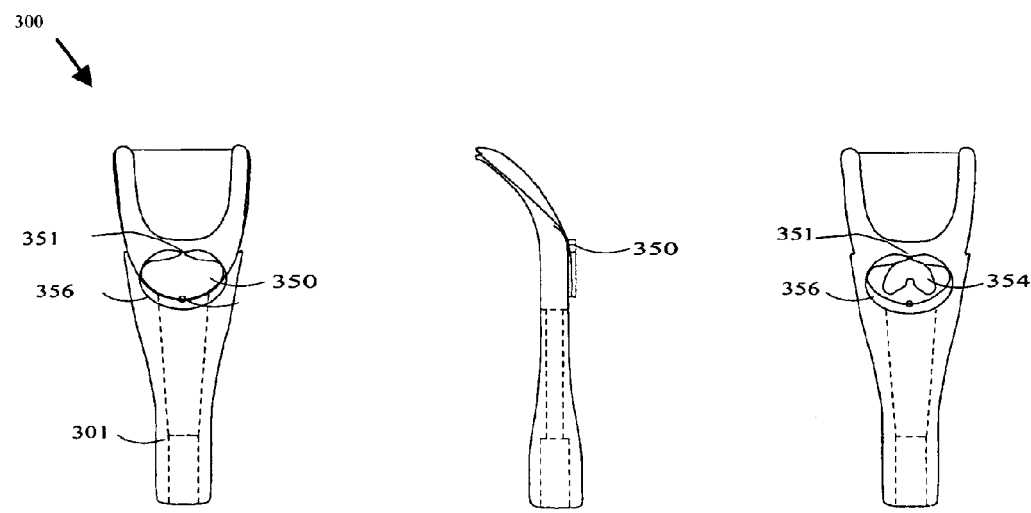
FIG. 3 shows a second embodiment of a disposable floss holder.

FIG. 3 shows a second embodiment of a disposable floss holder 300, in accordance with the present invention. The disposable floss holder 300 is shown in front, side, and back view. This disposable floss holder 300 has similar structure as the disposable floss holder 200 except that the pin-and-hole structure 251 is replaced with a narrow bridge structure 351 and the rotatable element 350 is modified from the rotatable element 250 accordingly. The rotatable element 350 is connected and rotatable with respect to the holder body 301 via this narrow bridge structure 351.

The material chosen for the disposable floss holder 300 shall be durable for bending back and forth over such a narrow bridge structure 351. Materials suitable for this purpose are known to those skilled in the art.

As shown in FIG. 3, the rotatable element 350 is coupled with an engagement element 354 that has a notch 353 to engage with the driving shaft 411. An opening 356 on the holder body 301 receives the engagement element 354 and allows the engagement element 354 to swing within a range with respect to the narrow bridge structure 351.

The holder body 301 with the rotatable element 350 can then be made with a single piece of plastic through mold injection process. Such a design simplifies the production process and reduces the production cost. As a result, the floss holder 300 can be better justified as a disposable item.

Figure 4:
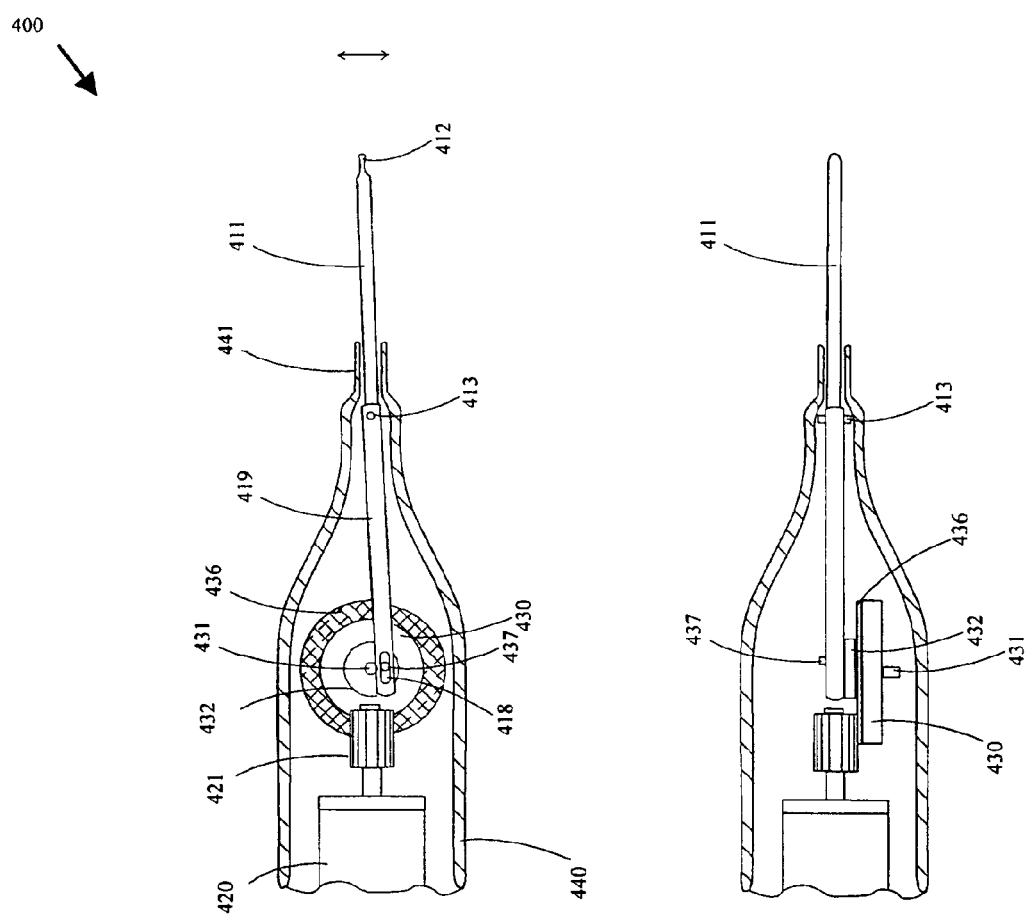
FIG. 4 shows a first embodiment of a driving handle.

FIG. 4 shows a first embodiment of a driving handle 400 of the automatic dental flosser 100, in accordance with the present invention. The driving handle 400 consists of a handle body 440 and a driving shaft 411. The handle body 440 houses a motor 420, a driving mechanism, and a battery or charger that is not shown in the Figure. The handle body 440 has an elongate shape and is such shaped to allow the user to grasp comfortably for dental flossing. The first end 441 of the handle body 440 is sized to fit into the hole 240 of the disposable floss holder 200. The first end 412 of the driving shaft 411 is shaped to fit with the notch 253 of the engagement element 254 of the disposable floss holder 200. In operation, the driving shaft 411 oscillates from side to side to drive the rotatable element 250 to swing back and forth with respect to the holder body 201 and to drag the loop of dental floss 210 to slide back and forth between the two tines 220 and 230.

As shown in FIG. 4, the driving mechanism includes a gear 421, a wheel 430, and a bar 419. The motor 420 drives the gear 421, which is coupled to the wheel 430 rotating around a shaft 431. The power coupling is through a layer of deformable material 436, e.g. rubber or soft plastic. Such a design is for its simplicity and low noise in comparison with typical gear coupling. The wheel 430 is concentric and affixed with a smaller wheel 432. A pin 437 is mounted on the smaller wheel 432 with an offset from the wheel's center, i.e., the shaft 431.

The bar 419 has a slot 418 at its first end and extends to the driving shaft 411 at its second end. The slot 418 is engaged into the pin 437 of the wheel 432. As the wheel 432 rotates, the pin 437 drives the bar 419 to swing back and forth around a pin 413, which is affixed on the handle body 440. Consequently, the bar 419 transfers the continuous rotation of the wheel 430 to a side-to-side oscillation of the driving shaft 411.

Preferably, the rotation speed of motor 420, the size of the gear 421, and the size of the wheel 430 are such chosen that the oscillation rate of the driving shaft 411 is about 30 to 50 Hz. The length of the driving shaft 411, the length of the bar 419, and the offset of pin 437 are such designed that the tip 412 of the driving shaft 411 has a side-to-side travel of about 2 to 3 mm.

Figure 5:
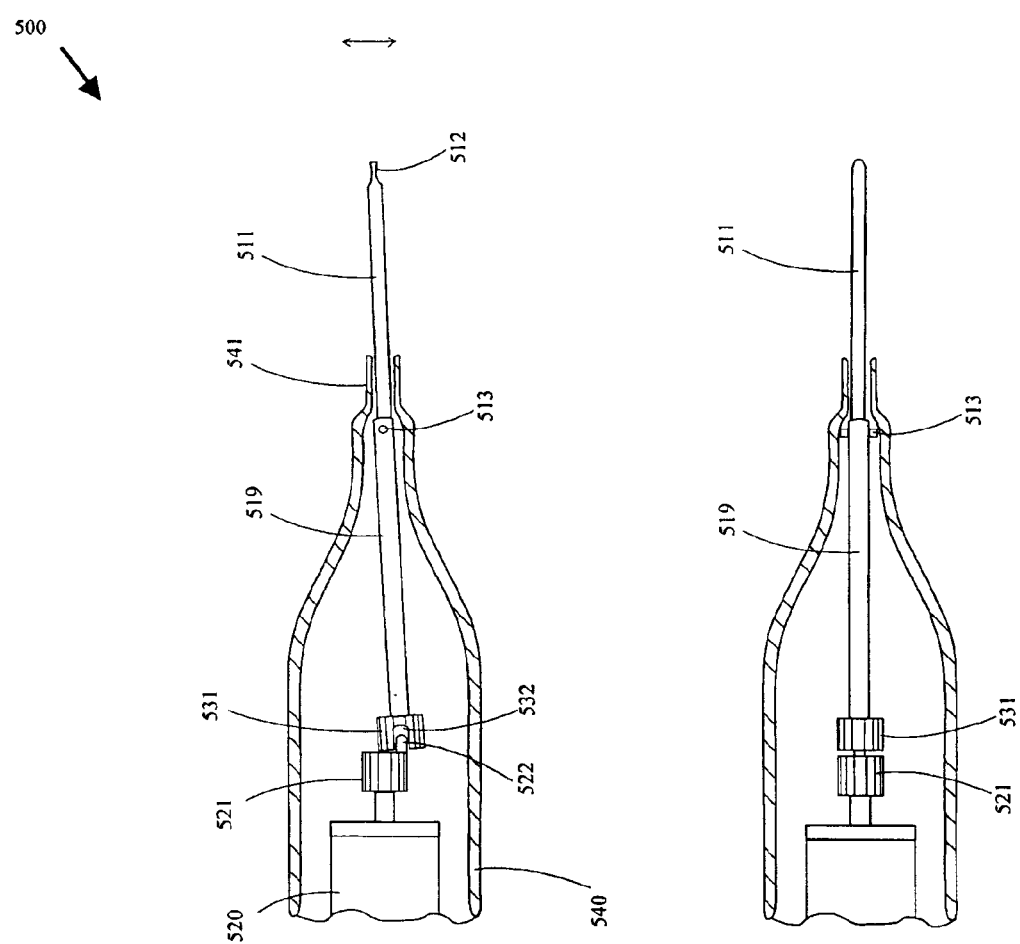
FIG. 5 shows a second embodiment of a driving handle.

FIG. 5 shows a second embodiment of a driving handle 500 of the automatic dental flosser 100, in accordance with the present invention. The construction of the driving handle 500 is similar to that of the driving handle 400 except the driving mechanism that couples the continuous rotation of the motor 520 to the side-to-side oscillation of the driving shaft 511.

As shown in FIG. 5, the driving mechanism includes a first disk 521, a second disk 531, and a bar 519. The first disk 521 is affixed on the motor's shaft and is mounted with an off-center pin 522. The second disk 531 is affixed on a first end of the bar 519 and is embedded a slot 532.

The motor 520 rotates the first disk 521 continuously. The off-center pin 522 slides inside the slot 532 and pushes the bar 519 to swing back and forth around a pin 513. Consequently, the driving mechanism transfers the continuous rotation of the motor 520 to a side-to-side oscillation of the driving shaft 511.

Preferably, the rotation speed of motor 520 is such chosen that the oscillation rate of the driving shaft 511 is about 50 to 100 Hz. The length of the driving shaft 511, the length of the bar 519, and the offset of pin 522 are such designed that the tip 512 of the driving shaft 511 has a side-to-side travel of about 2 to 3 mm.

Figure 6:
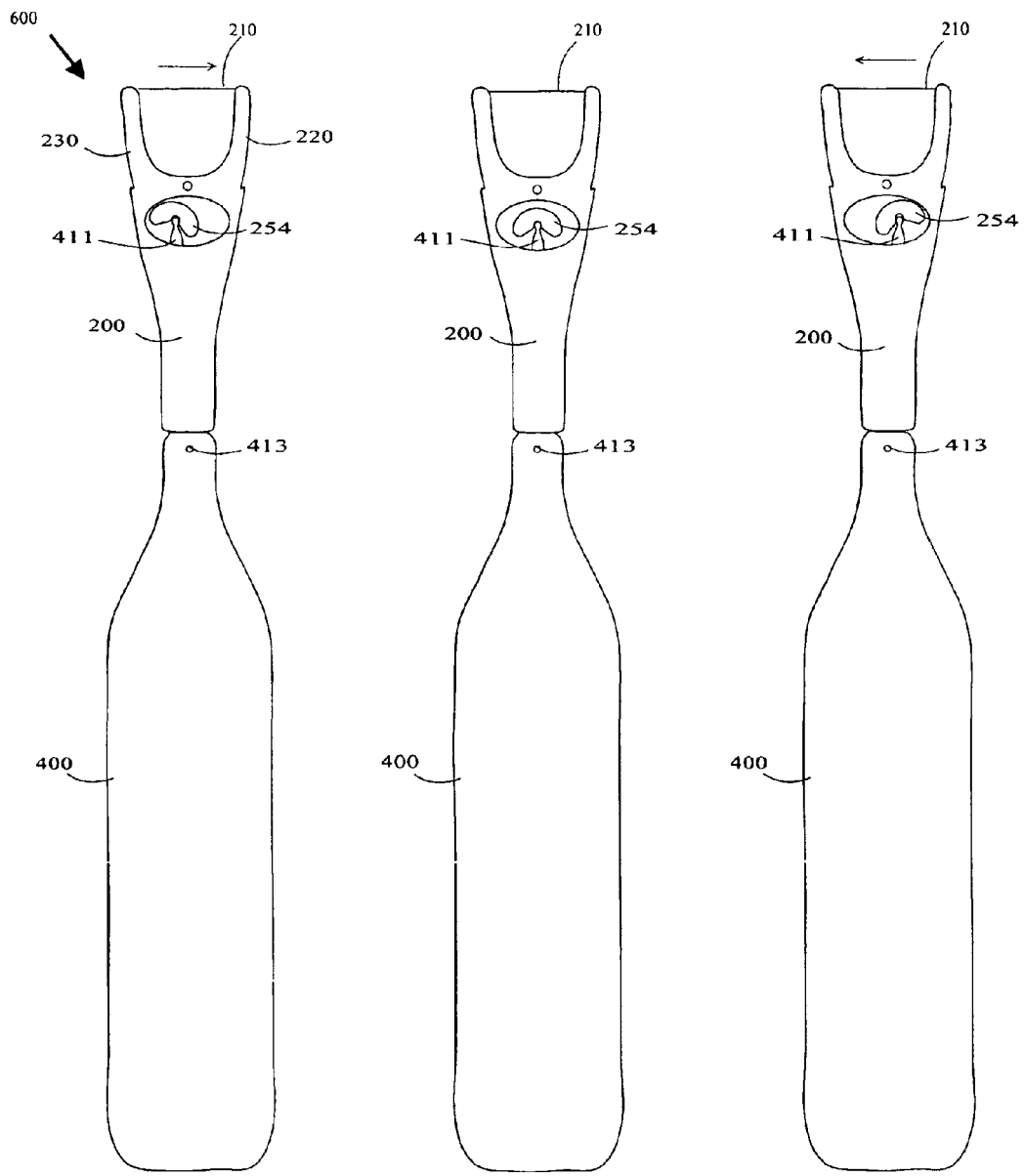
FIG. 6 shows an automatic dental flosser with the driving shaft at different angle positions.

FIG. 6 shows an automatic dental flosser 600 with the driving shaft 411 at different angle positions. The automatic dental flosser 600 is shown in a back view of the floss holder 200. The driving shaft 411 is engaged with the notch 253 on the engagement element 254. As the driving shaft 411 oscillates from side to side, it drives the engagement element 254 and thus the rotatable element 250 to swing back and forth with respect to the floss holder 200. The rotatable element 250 drives in turn the loop of dental floss 210 to slide back and forth between the two tines 220 and 230.

The size of the rotatable element 250 and the distance from the notch 253 to the rotation center 251 shall be such chosen that the dental floss 210 has a side-to-side travel of about 4 to 8 mm.

Figure 7:
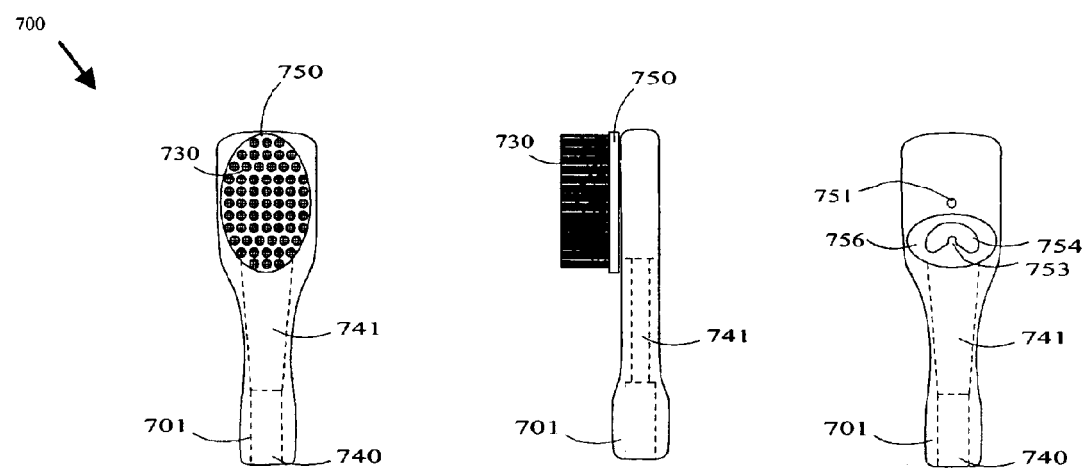
FIG. 7 shows a first embodiment of an attachable toothbrush head.

FIG. 7 shows a first embodiment of a toothbrush head 700, in accordance with the present invention. The toothbrush head 700 is shown in front, side, and back view. The toothbrush head 700 consists of a toothbrush head body 701 and a rotatable bristle holder 750. Toothbrush bristles 730 are implanted on the rotatable bristle holder 750, which is in turn mounted on the first end of the toothbrush head body 701 and is operationally rotatable around a pin-and-hole structure 751.

As shown in the back view of the toothbrush head 700, the rotatable bristle holder 750 is affixed with an engagement element 754, which has a notch 753 to engage with the driving shaft 411. There is an opening 756 on the toothbrush head body 701 to receive the engagement element 754 and to allow the engagement element 754 to rotate within a range around the pin-and-hole structure 751.

There is a mounting hole 740 in the second end of the toothbrush head body 701. This hole 740 is used to attach the toothbrush head 700 onto the driving handle 400. There is also a hole 741 connecting between the mounting hole 740 and the opening 754. This hole 741 enables the driving shaft 411 of driving handle 400 to engage with the notch 753 of the engagement element 754 so as to drive the rotatable bristle holder 750. When the rotatable bristle holder 750 is driven to rotate back and forth around the pin-and-hole structure 751, the bristles 730 wipes back and forth for tooth brushing.

Figure 8:
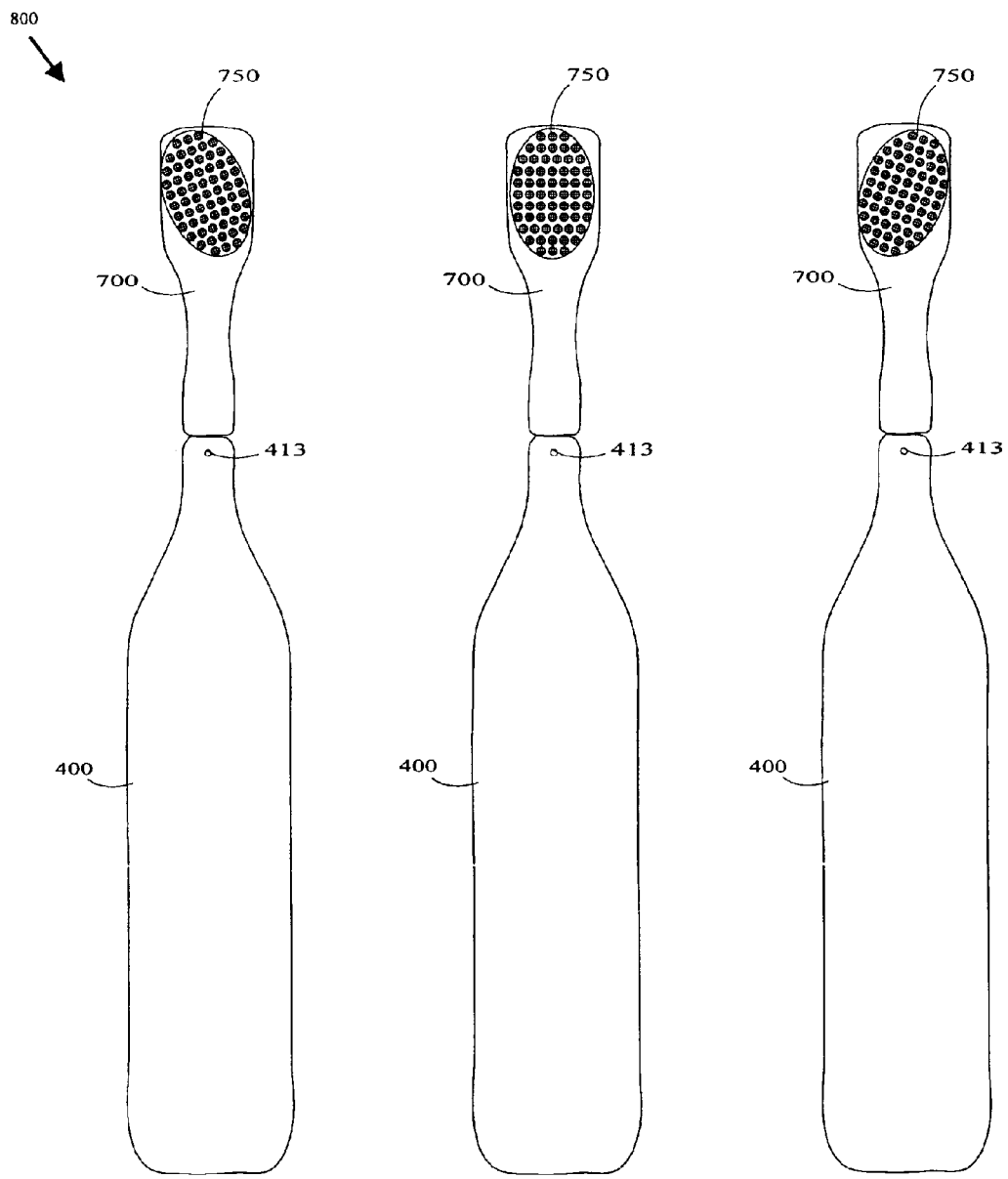
FIG. 8 shows an automatic toothbrush with the driving shaft at different angle positions.

FIG. 8 shows an automatic toothbrush 800 with a toothbrush head 700 at different angle positions of the driving shaft 411. The automatic toothbrush 800 is shown in a front view of the toothbrush head 700. The driving shaft 411 is engaged with the notch 753 on the engagement element 754. As the driving shaft 411 oscillates from side to side, it drives the rotatable bristle holder 750 to rotate and thus the bristles 730 to wipe back and forth for tooth brushing.

The size of the rotatable disk 750 and the distance from the notch 753 to the rotation center 751 shall be such chosen that the toothbrush bristles 730 have a back and forth travel distance up to 4 to 8 mm.

Figure 9:
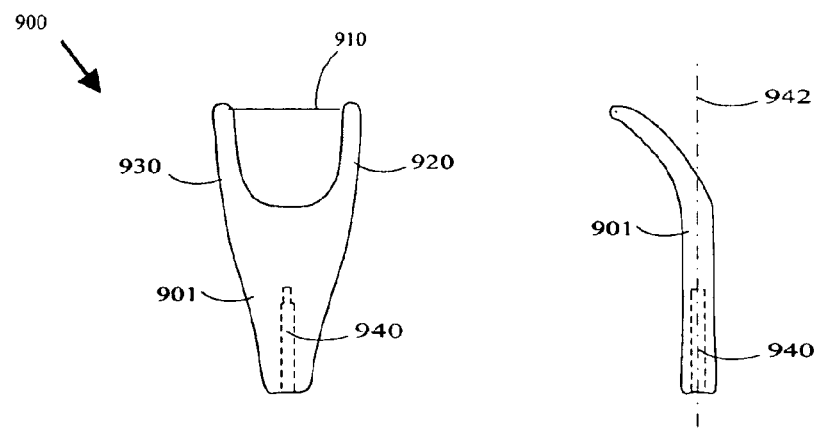
FIG. 9 shows a third embodiment of a disposable floss holder.

FIG. 9 shows a third embodiment of a disposable floss holder 900, in accordance with the present invention. The floss holder 900 has on its first end two tines 920 and 930 securing a piece of dental floss 910 and on its second end a mounting hole 940. The two tines 920 and 930 are such shaped and bent to hold the piece of dental floss 910 perpendicular to and about 5 to 20 mm away from an axis 942 of the mounting hole 940. The two tines 920 and 930 are further bent and spaced to have the piece of dental floss 910 a length of about 10 to 20 mm. The mounting hole 1040 is sized to fit the driving shaft 411 of the driving handle 400.

Figure 11:
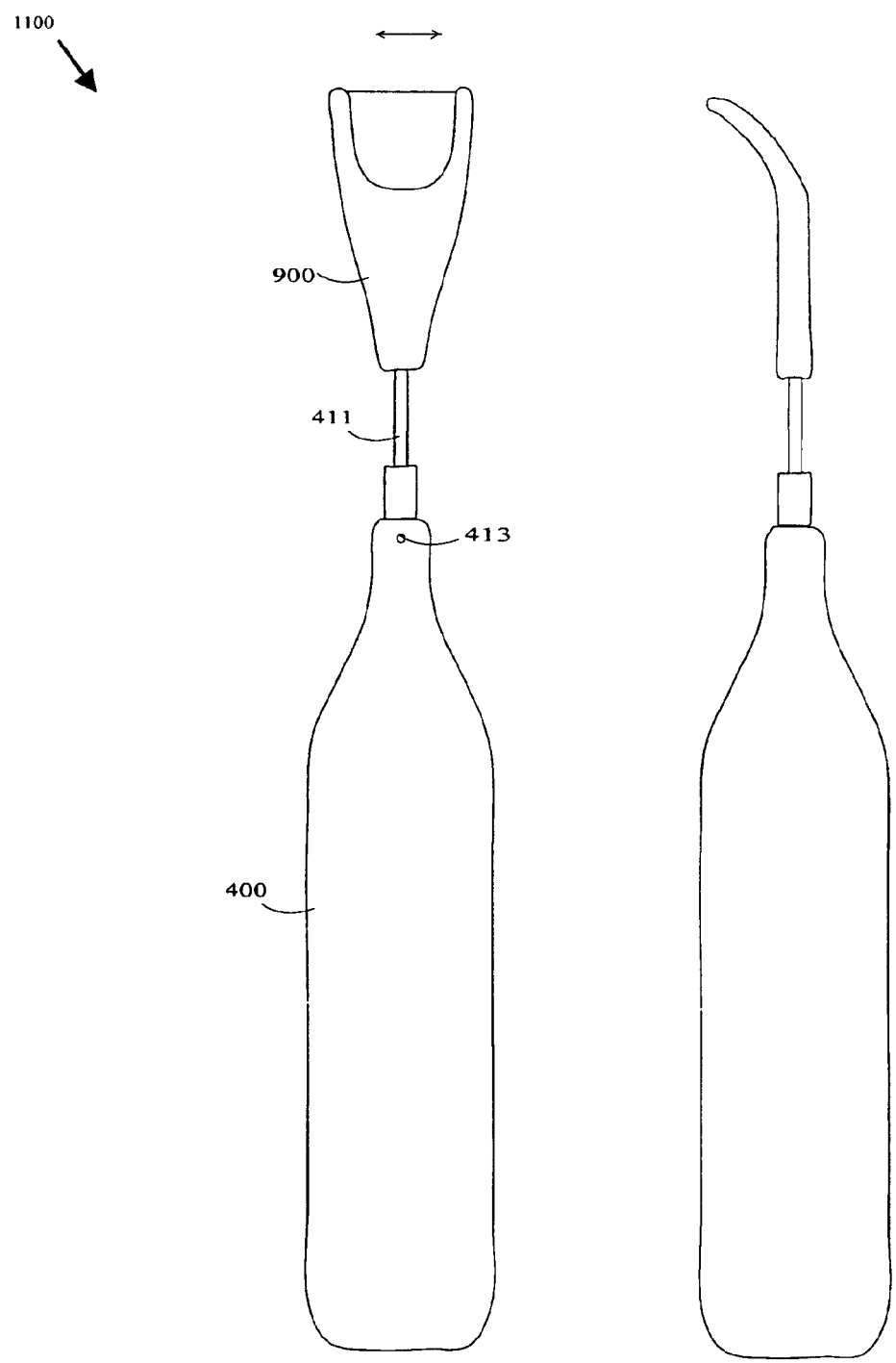
FIG. 11 shows an automatic dental flosser employing a disposable floss holder of FIG. 9.

FIG. 11 shows an automatic dental flosser 1100 with a disposable floss holder 900, in accordance with the present invention. The automatic dental flosser 1100 consists of a disposable floss holder 900 fastened onto the driving shaft 411 of a driving handle 400. As the driving shaft 411 swings from side to side around the pin 413, the floss holder 900 moves back and forth for dental flossing.

The length of the disposable floss holder 900 is chosen such that the travel distance of the floss 910 is up to preferably 4 to 6 mm. For a preferred embodiment, the peak-to-peak oscillation amplitude of the tip 412 of the driving shaft 411 is about 2 to 3 mm and the length of the driving shaft 411 is about 40 mm, the length of the disposable floss holder 900 is approximately 50 mm.

Figure 10:
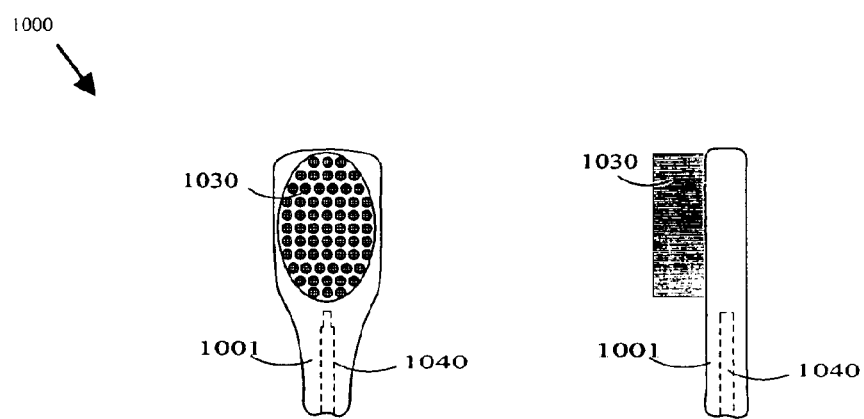
FIG. 10 shows a second embodiment of a toothbrush head.

FIG. 10 shows a second embodiment of an attachable toothbrush head 1000, in accordance with the present invention. The toothbrush head 1000 has bristles 1030 implanted on its first end and a mounting hole 1040 on its second end. The mounting hole 1040 is sized to fit the driving shaft 411 of the driving handle 400.

Figure 12:
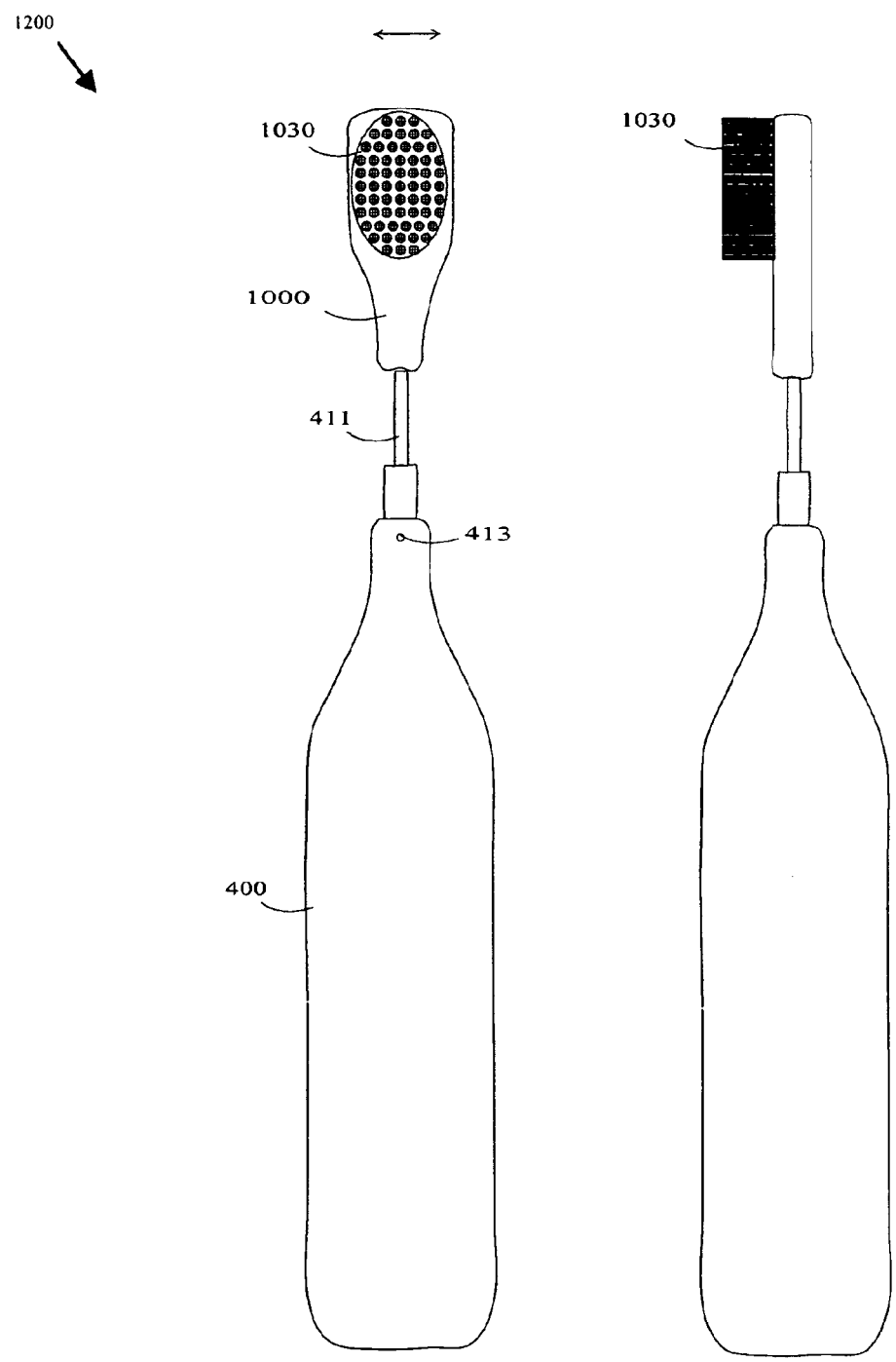
FIG. 12 shows an automatic toothbrush employing a toothbrush head of FIG. 10.

FIG. 12 shows an automatic toothbrush with a toothbrush head 1000, in accordance with the present invention. The automatic toothbrush 1200 consists of a detachable toothbrush head 1000 fastened onto the driving shaft 411 of a driving handle 400. As the driving shaft 411 swings from side to side around the pin 413, the toothbrush head 1000 wipes back and forth for tooth brushing.

The length of the detachable toothbrush head 1000 is such chosen that the travel distance of the toothbrush bristles 1030 is preferably 4 to 6 mm. For a preferred embodiment, the peak-to-peak oscillation amplitude of the tip 412 of the driving shaft 411 is about 2 to 3 mm and the length of the driving shaft 411 is about 40 mm, the length of the detachable toothbrush head 1000 is approximately 50 mm.

The floss holder 900, as well as the floss holders 200 and 300, adapts the shape of the tines from a popular manual floss holder that is relatively easy to manipulate. The floss holder 900 is simple and easy to make, and it is thus better justified to be a disposable item.

The automatic toothbrush 800 adapts a circular oscillation of the toothbrush bristles 730. Such a circular oscillation has been well accepted in the market.

The driving handles 400 and 500 implement a side-to-side oscillation of the driving shaft to enable the automatic dental flossers 100 and 1100 and automatic toothbrushes 800 and 1200. Any combination of these automatic dental flossers and toothbrushes can be a useful product.

It is understood that floss holder 200 and toothbrush head 700 adapt a similar circular oscillation of a rotatable member. Therefore, other driving mechanism or coupling mechanism that can provide a circular oscillation to a toothbrush head can also be used to drive a floss holder with a rotatable element.

It is also understood that dental flosser 1100 and toothbrush 800 adapt a hybrid motion, of which the floss holder is driven to swing side to side while the toothbrush bristles are driven to oscillate rotationally. Other than the driving shafts and driving mechanisms described in FIGS. 4 and 5, there are driving mechanisms that can provide similar hybrid motion or provide movements including such a hybrid motion.

Figure 13:
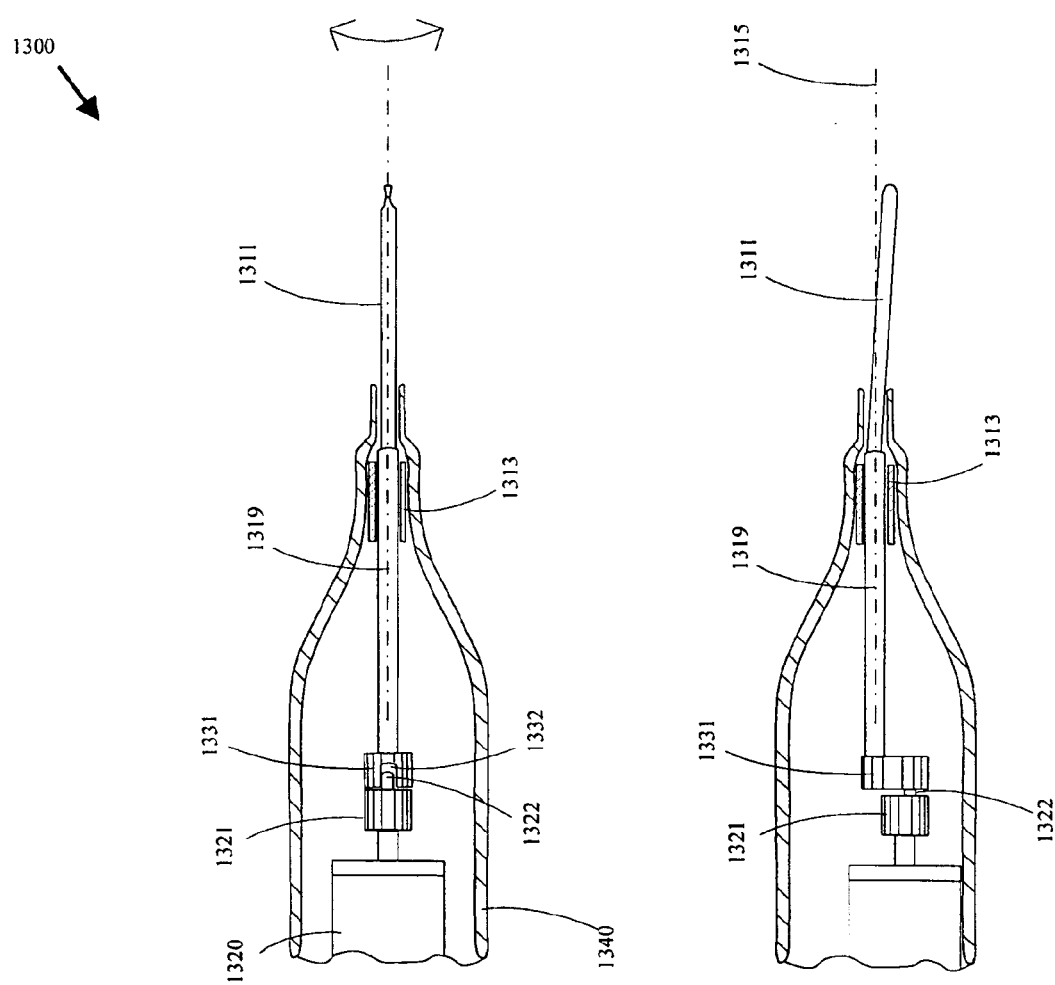
FIG. 13 shows a third embodiment of a driving handle.

For example, FIG. 13 shows a third embodiment of a driving handle 1300 that is suitable to provide a hybrid motion for dental flossing and tooth brushing, in accordance with the present invention. The construction of the driving handle 1300 is similar to that of the driving handle 400 except the driving mechanism that couples the continuous rotation of the motor 1320 to a side-to-side swing oscillation of the driving shaft 1311.

As shown in FIG. 13, the driving mechanism includes a disk element 1321, an arm element 1331, and a bar 1319. The disk 1321 is affixed on the motor's shaft and is mounted with an off-center pin 1322. The arm element 1331 is affixed on a first end of the bar 1319 and is embedded a slot 1332. The motor 1320 rotates the disk element 1321 continuously. The off-center pin 1322 slides inside the slot 1332 and pushes the bar 1319 to rotate back and forth around a bearing 1313. Consequently, the driving mechanism transfers the continuous rotation of the motor 1320 to a rotational oscillation of the driving shaft 1311 around an axis 1315.

When a floss holder 900 is fastened on the driving shaft 1311, the driving handle 1300 can drive the floss holder 900 to swing from side to side around an axis 1315 of the driving handle 1300. When a toothbrush head 700 is attached onto the driving handle 1300, the driving shaft 1311 can drive the toothbrush bristles 730 to oscillate rotationally with respect to the toothbrush head 700. Consequently, the driving handle 1300 provides a hybrid motion for dental flossing and tooth brushing.

Therefore, it is further understood that, the present disclosure includes only a few embodiments, other modifications and variations may be made without departing from the following claims.

What is claimed is:

1. A dental device comprising:
    a floss holder having an elongate shape with a first end and a second end and having on its first end two tines holding a piece of dental floss and on its second end a fastening element, wherein said two tines are such shaped and bent that said piece of dental floss is held approximately perpendicular to and about 5 to 20 mm away from an axis of said second end;
    a driving handle housing a motorized driving mechanism and having on its first end a driving element and a mounting element, wherein said driving element is driven by said driving mechanism to swing from side to side around an axis affixed on said driving handle, wherein said driving element oscillates at a frequency about 50 to 100 Hz and is confined not to move up and down, and wherein said driving handle has an elongate shape for easy hand holding and said mounting element is secured with said driving handle;
    wherein said floss holder is coupled to said driving handle and said driving element drives said piece of dental floss to oscillate with respect to said driving handle, wherein said piece of dental floss moves from side to side for dental flossing.

2. A dental device of claim 1 further comprising:
    a toothbrush head interchangeable with said floss holder, wherein said toothbrush head has an elongate shape and has on its first end a rotatable disk implanted with toothbrush bristles and on its second end an attachment element, wherein said rotatable disk is coupled with an engagement element and is rotatable with respect to said toothbrush head, and wherein said toothbrush bristles can wipe back and forth as said rotatable element is driven via said engagement element to oscillate roatationally;
    wherein, when said toothbrush head replaces said floss holder, said toothbrush head is attached and secured onto said mounting element of said driving handle and said driving element is engaged with said engagement element of said rotatable disk to drive said rotatable disk to oscillate rotationally, wherein said toothbrush bristles wipe rotationally back and forth for tooth brushing.

3. A dental device of claim 1 wherein said floss holder is a disposable item made from a single piece of plastic.

4. A dental device of claim 1 wherein said floss holder as also packaged as a separated product.

5. A dental device of claim 1 wherein said fastening element of said floss holder consists of a hole shaped to fit said driving element of said driving handle.

6. A dental device of claim 1 wherein said piece of dental floss is driven to move from side to side with an amplitude of approximately 4 to 6 mm.

7. A dental device of claim 1 wherein said driving element is a driving shaft.

8. A dental device of claim 1 wherein said driving mechanism employs an off-center pin and a sliding slot.

9. A dental device of claim 1 wherein said piece of dental floss is affixed on said two tines and said driving element drives said floss holder to swing from side to side with said piece of dental floss for dental flossing.

10. A dental device of claim 1 wherein said piece of dental floss is held by said two tines via a slot on tip of each of said two tines and said floss holder remains stationary while said driving element drags said piece of dental floss to slide between said two tines for dental flossing.

11. A dental device of claim 1 wherein said floss holder has a rotatable element fastening two ends of said piece of dental floss, wherein said rotatable element is coupled to and driven by said driving element to oscillate rotationally, and wherein said piece of dental floss is dragged to slide back and forth between said two tines for dental flossing.

12. A dental device, comprising:

a floss holder having an elongate shape with a first end and a second end and having on its first end two tines securing a piece of dental floss and on its second end a fastening element, wherein said two tines are such shaped and bent that said piece of dental floss is held approximately perpendicular to an axis of said second end and that said two tines are spaced preferably 15 to 20 mm apart;

a driving handle housing a motorized driving mechanism and having on its first end a driving shaft and a mounting element, wherein said motorized driving mechanism employing an off-center pin and a sliding slot to drive said driving shaft to oscillate around an axis defined in said driving handle and said driving shaft is confined not to move up and down, and wherein said off-center pin and said sliding slot convert a rotational motion directly to a sinusoidal oscillation of said driving shaft;

wherein said floss holder is attached and fastened onto said driving shaft of said driving handle via said fastening element, and wherein said floss holder is driven to oscillate from side to side with respect to said driving handle and thus said piece of dental floss is driven to move from side to side to accomplish dental flossing.

13. A dental device of claim 12 wherein said floss holder is a disposable item made from a single piece of plastic and is packaged as a separated product.

14. A dental device of claim 12 further comprising:

a toothbrush head interchangeable with said floss holder, wherein said toothbrush head has an elongate shape and has on its first end a rotatable disk implanted with toothbrush bristles and on its second end an attachment element, wherein said rotatable disk is coupled with an engagement element such that said rotatable disk can be driven via said engagement element to oscillate rotationally, with respect to said toothbrush head;

wherein when said toothbrush head replaces said floss holder, said attachment element of said toothbrush head is attached and secured onto said mounting element of said driving handle and said driving shaft of said driving handle is engaged with said engagement element of said rotatable disk, and wherein said rotatable disk is driven to oscillate rotationally with respect to said toothbrush head and thus said toothbrush bristles is driven to wipe rotationally back and forth to accomplish tooth-brushing.

15. A dental device of claim 12 wherein said piece of dental floss is driven to move from side to side with an amplitude of approximately 4 to 6 mm.

16. A dental device of claim 12 wherein said driving shaft oscillates at a frequency of 50 to 100 Hz.

17. A dental device of claim 12 wherein said two tines are such shaped and bent that said piece of dental floss is held approximately perpendicular to and about 5 to 20 mm away from an axis of said second end.

* * * * *